(12) United States Patent
Saini

(10) Patent No.: US 7,144,735 B2
(45) Date of Patent: Dec. 5, 2006

(54) ELECTRODIALYSIS METHOD AND APPARATUS FOR TRACE METAL ANALYSIS

(75) Inventor: Harmesh K. Saini, Santa Clara, CA (US)

(73) Assignee: Metara, Inc., Sunnyvale, CA (US)

( * ) Notice: Subject to any disclaimer, the term of this patent is extended or adjusted under 35 U.S.C. 154(b) by 231 days.

(21) Appl. No.: 10/655,966

(22) Filed: Sep. 5, 2003

(65) Prior Publication Data

US 2005/0051485 A1    Mar. 10, 2005

(51) Int. Cl.
G01N 30/96 (2006.01)
G01N 33/20 (2006.01)
B01D 57/02 (2006.01)
B01D 11/04 (2006.01)

(52) U.S. Cl. .................. 436/73; 204/520; 204/539; 210/638; 210/639; 210/644; 436/171; 436/178

(58) Field of Classification Search ............... 210/638, 210/639, 650, 651, 656, 748, 644, 683, 684; 436/73–84, 171, 178; 204/630, 520, 539, 204/629
See application file for complete search history.

(56) References Cited

U.S. PATENT DOCUMENTS

| | | | |
|---|---|---|---|
| 4,584,276 A * | 4/1986 | Hanaoka et al. ............. 436/150 |
| 4,999,098 A * | 3/1991 | Pohl et al. .................. 210/670 |
| 5,174,872 A * | 12/1992 | Scott .......................... 205/779 |
| 5,414,259 A * | 5/1995 | Kingston ..................... 250/283 |
| 5,518,622 A | 5/1996 | Stillian et al. ............... 210/635 |
| 5,597,481 A | 1/1997 | Stillian et al. ........... 210/198.2 |
| 6,030,844 A | 2/2000 | Hase |
| 6,296,760 B1 | 10/2001 | Petty et al. |
| 2005/0202563 A1* | 9/2005 | Dasgupta et al. ............. 436/52 |

* cited by examiner

Primary Examiner—Joseph Drodge
(74) Attorney, Agent, or Firm—Jonathan W. Hallman; MacPherson Kwok Chen & Heid LLP

(57) ABSTRACT

An electrodialysis method and apparatus are provided for treating a sample including trace metals in a matrix. Advantageously, the present invention allows for highly accurate detection of trace contaminants in a solution sample, in particular trace metals, substantially in real-time and on-line. The present invention includes flowing a carrier solution through a carrier solution channel separated from a sample channel by a membrane. A component of the carrier solution is diffused through the membrane into the sample channel to stabilize trace metals in the solution sample for subsequent analysis. Simultaneously, the matrix is eliminated, neutralized, and/or modified for enhanced analysis.

20 Claims, 13 Drawing Sheets

```
' $Workfile: Memberane. config $ membrane_A_enable = 1
membrane_D_enable = 1 membrane.sensor.antibubble.retry=10          ' # of times to requery optical sensor when air is detected
membrane.sensor.antibubble.retry.delay= 1    ' delay (seconds) between requeries of sensor when air is
detected ' Solution used with membrane membrane_A_solutionname = HF
membrane_D_solutionname = H2SO4

' HF

HF_operating_vol = 1600          'implied volume of solution in syringe before membrane operation
begins
HF_carrier_solution = HF         '? no consequence
HF_carrier_syr_speed = 10        '? no consequence
HF_refill_speed = 30             'speed to draw from reservoir back to the syringe HF_stage1_neutralization_speed = 10   'speed to push through membrane, in microliters/sec
HF_stage1_cycles = 2                  'times to repeat this run
HF_stage1_current = 250               'milliamps
HF_stage1_polarity = 0                '-1 = oscillate, 0 = negative, 1 = positive HF_stage2_cycles = 2
HF_stage2_polarity = 0
HF_stage2_neutralization_speed = 10
HF_stage2_current = 200

UPW_clean_num_cycles=2
UPW_clean_refill_speed=30        'speed UPW is drawn from resevoir to syringe
UPW_clean_neut_speed=10          'speed UPW is run through the membrane HF_num_stages=2          'increment this, and add additional HF_stageX parameters to have more stages
```

FIG. 8 ns and can change over time. Thus, by the time a sample reaches a laboratory for analysis, the sample may not be in exact formulation as it was at the time of collection.

ELECTRODIALYSIS METHOD AND APPARATUS FOR TRACE METAL ANALYSIS

BACKGROUND OF THE INVENTION

1. Field of Invention

The present invention generally relates to analysis of solutions. More particularly, the present invention relates to on-line automated matrix elimination, neutralization, or modification for trace contaminant analysis of solutions.

2. Discussion of the Related Art

Chemical solutions are used in various manufacturing processes in a multitude of industries, including the semiconductor, environmental, and pharmaceutical industries. A solution sample includes a matrix, defined herein as a liquid solution, suspension, or colloid, and a detectable amount of at least one analyte of interest. Examples of matrixes are diluted or concentrated acids, bases, oxidants, reducing reagents, solvents (such as alcohols, esters, ethers, glycols, ketones, amides, amines, or their mixtures), cleaning solutions, photoresists, strippers, and developers. Examples of analytes of interest are metals and their species.

The matrix has a pronounced effect on the quantification of trace constituents by modern analytical instruments. For example, a common problem is detecting analytes of interest in a matrix including one or more compounds of high ionic strength. Many times, the desired analyte peaks or signals are obscured by the large interfering peak of an undesired matrix ion. In many analytical instruments, the detector is saturated with matrix ion signals and is not able to distinguish the desired analyte signal.

In some cases, the desired signal is suppressed because the matrix ions compete with the desired analyte ions when ionization of the sample occurs for analysis purposes. Furthermore, matrix ions are increased during ion formation in electrospray ionization because in most cases, the matrix ions solvate or deprotonate the analyte of interest, resulting in less ion formation of the analyte of interest.

The composition or properties of a matrix may also change from process to process and during the life of the sample, which may then affect the recovery of an analyte from a complex matrix. Analyte speciation may further compound this effect. The stability of a sample/analyte may also change during analysis because of a changing thermal regime or photolytic effect. Thus, inaccurate analysis of a sample may occur because of the transitory nature of the matrix.

However, in many instances, accurately monitoring the analytes of a sample at a specific point in time during a process is highly desirable. For example, in semiconductor manufacturing processes, monitoring the elemental and molecular composition of solutions is of immense importance for producing reliable devices with high yield. Purity of these solutions during offline and online processes is very important as well. The continuous decrease in the geometry of devices requires increased control of the contaminants in solution, especially those solutions that come in direct contact with the electronic circuitry during device fabrication.

To reliably measure the elemental and molecular composition of samples at a parts-per-trillion level is not only complicated but also laborious and time consuming. The biggest challenge is to maintain the integrity of the sample starting from the sampling (i.e., collection) to the end of the analysis.

First, most matrixes are dynamic in nature, i.e. the components of a solution continually react with other components and can change over time. Thus, by the time a sample reaches a laboratory for analysis, the sample may not be in exact formulation as it was at the time of collection.

Second, many matrixes are strong absorption media for airborne soluble contaminants so if samples are exposed to air at any stage during sampling, transportation, or analysis, the matrix of the sample may be altered or contaminated.

Third, the cleanliness of the sampling containers is very important and a large amount of time and money is spent to clean sampling containers. The amount of time the sample is allowed to sit in the sampling container before being analyzed can also effect the analysis outcome. It has been reported that even the cleanest of sampling containers can leach out many undesirable contaminants.

Fourth, offline elimination, neutralization, or modification of matrixes generally pose a high risk of contamination that can affect the integrity of the sample for the reasons stated above.

At present, for routine monitoring of matrixes, samples are collected from sources in a protected clean environment in pre-cleaned containers. The containers holding the samples are delivered to the laboratory for measurements of the elemental or molecular constituents by various analytical instruments. It can take between 4 to 24 hours before the analysis results are received by process personnel. Accordingly, in most cases, if a problem is detected, such as impurities in the sample, processing of defective product will have occurred for some time and the cost related to low yield will be high. As a result, many industries are placing a major emphasis on on-line measurements to provide substantially real-time analysis.

In common practice, depending on the nature and concentration of the matrix, various analytical laboratories have developed their own methods to test these matrixes. For example, some laboratories dilute the sample to reduce the effect of the matrix but by doing so many ultra low trace level contaminants may not be detected. Other laboratories eliminate the matrix by heat and/or evaporation but by doing so potentially lose the integrity of the sample constituents.

Therefore, a need exists for a method and apparatus for accurate elemental and molecular analysis of process solutions, particularly for trace metal contaminants.

SUMMARY

The present invention provides a method and apparatus for treating a solution sample including trace contaminants in a matrix, allowing for accurate and substantially real-time analysis of the sample. The solution sample is treated to stabilize trace metals in solution while also neutralizing, modifying, and/or eliminating the matrix.

In accordance with one embodiment of the present invention, a method of analyzing trace metals in solution is provided. The method includes providing a sample channel separated from a carrier solution channel by an ion exchange membrane, and flowing a sample through the sample channel. The sample includes a matrix and at least one trace metal to be detected. The method further includes providing an electrical potential to assist diffusion of ions through the ion exchange membrane. Further, the method includes flowing a carrier solution through the carrier solution channel so that a component of the carrier solution is diffused through the ion exchange membrane into the sample channel to treat the sample for detection of the at least one trace metal.

In accordance with another embodiment of the present invention, a method of analyzing trace metals in solution includes providing a sample channel between two carrier solution channels, the sample channel being defined by two ion exchange membranes that separate the sample channel from the two carrier solution channels. The method further includes flowing a carrier solution including a metal-complexing reagent through at least one of the two carrier solution channels so that the metal-complexing reagent is diffused through at least one of the ion exchange membranes into the sample channel. A metal complex is advantageously formed between the metal-complexing reagent and the trace metal to stabilize the trace metal in solution and prevent precipitation of the metal, thereby treating the sample for subsequent analysis.

In accordance with yet another embodiment of the present invention, a method of analyzing trace metals in solution includes flowing a carrier solution including hydroxide or hydronium ions through a carrier solution channel. The hydroxide or hydronium ions are diffused through an ion exchange membrane into the sample channel to substantially neutralize an acidic or basic matrix while the metal-complexing reagent and the trace metal also form a metal complex in solution, thereby treating the sample for more accurate subsequent analysis.

Advantageously, the present invention provides an efficient and highly accurate method and apparatus for detecting trace contaminants in a solution sample. In particular, the present invention is highly advantageous when attempting to detect trace metal contaminants. Trace metals are stabilized in solution and do not precipitate out of the solution, thereby allowing for and/or greatly enhancing subsequent analysis. Also, the matrix is substantially neutralized, eliminated, and/or modified at the same time as the metals are stabilized, further enhancing subsequent analysis of the solution sample.

These and other features and advantages of the present invention will be more readily apparent from the detailed description of the embodiments set forth below taken in conjunction with the accompanying drawings.

BRIEF DESCRIPTION OF DRAWINGS

FIG. 8 is an example of a configuration file for operating an apparatus for analyzing trace metals, in accordance with an embodiment of the present invention.

Use of the same or similar reference symbols in different figures indicates identical or similar items. It is further noted that the drawings may not be drawn to scale.

DETAILED DESCRIPTION

Figure 1:
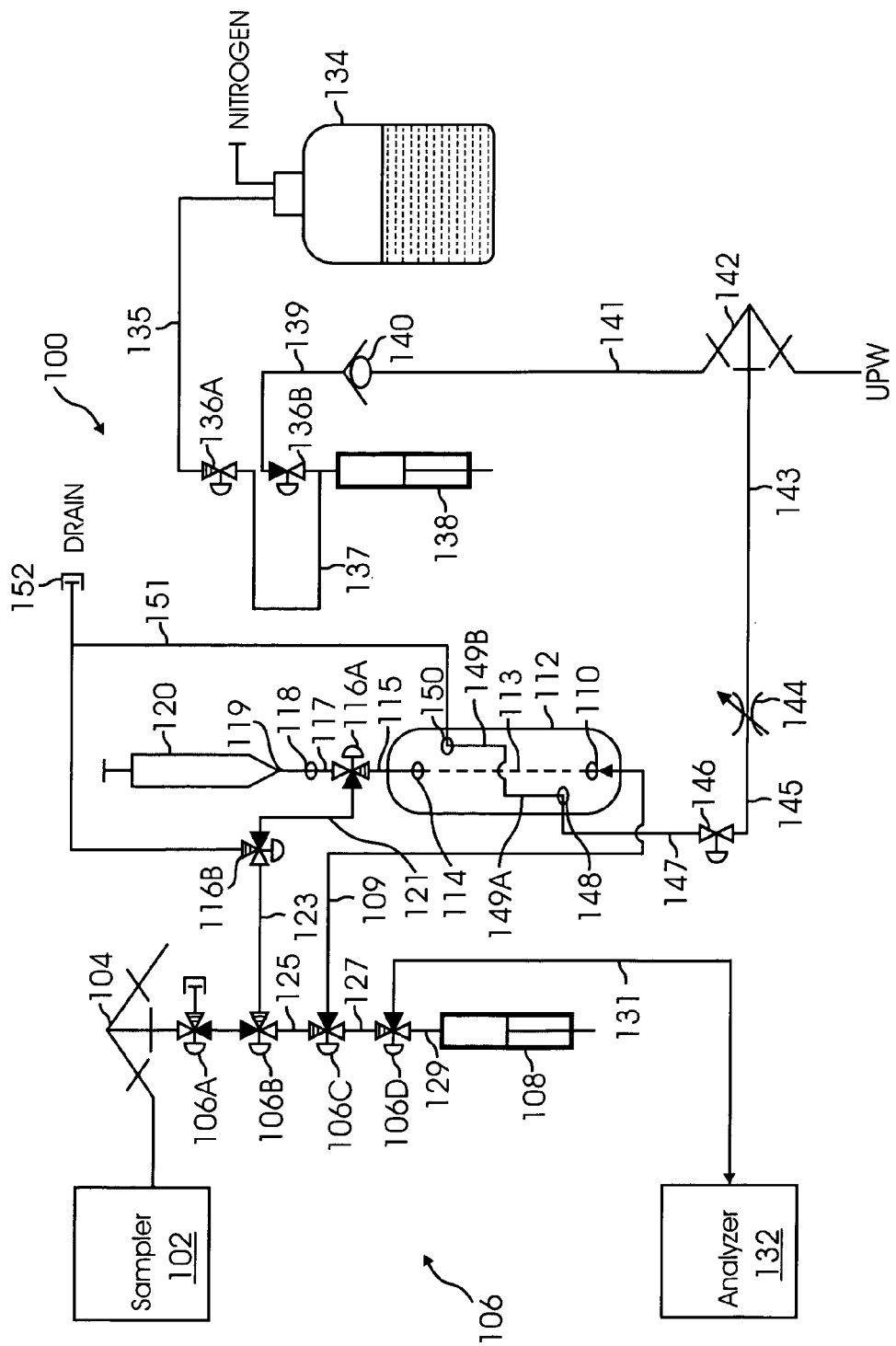
FIG. 1 shows a block diagram illustrating an apparatus for analyzing trace metals, in accordance with an embodiment of the present invention.

The present invention uses the principles involved in a technique known as "diffusion dialysis". Diffusion dialysis is a membrane separation method in which the components of matrixes move across a membrane depending on the nature of the membrane and purpose of separation. For example, solutes of high concentration permeate through the membrane towards low concentration under the influence of a concentration gradient. If the membrane is chemically functionalized with anion exchange groups, the membrane will allow only anions, negatively charged ions, to pass. Similarly, if the membrane is chemically functionalized with cation exchange groups, the membrane will allow only cations, positively charged ions, to pass. In other embodiments, the membrane is functionalized to be selective for desired chemical groups.

Since diffusion dialysis tends to be a very slow process, a separation process known as "electrodialysis" is used in the present invention. Electrodialysis is a separation method in which ions are transported through an ion permeable membrane from/to a sample solution to/from a carrier solution under the influence of an electric potential gradient which increases the speed of ion movement. The electrodialysis membrane has the ability to selectively permeate ions having positive or negative charge and retain ions of opposite charge. The speed of ion transportation across the membrane is a function of current applied to electrodes providing the electric potential gradient.

Even though electrodialysis is a very efficient, fast, and clean technique for eliminating, neutralizing, or modifying matrixes, the technique has not been previously used to detect trace metals in solution because the metals tend to precipitate inside the membrane when undergoing conventional electrodialysis. During conventional electrodialysis, hydroxide ions ($OH^-$) are produced at the cathode electrode and migrate into the sample channel where they react with metals to form salts that may precipitate on the membrane. For example, most of the transition metals tend to form insoluble metal-oxide (MO) or metal-hydroxide (MOH) precipitates near the neutral pH. Furthermore, most of the metals that form salts are lost during neutralization of a sample matrix by conventional electrodialysis.

To analyze trace metals by analytical instruments, it is important to keep the metals in solution. This can be accomplished either by maintaining a pH away from neutral (i.e., a lower pH (acidic) or higher pH (basic)) and/or by stabilizing the metals in solution by forming metal complexes.

In accordance with an embodiment of the present invention, a method and apparatus are provided utilizing the technique of electrodialysis to eliminate, neutralize, and/or modify the matrix of a solution sample while simultaneously stabilizing metals in solution to allow detection of trace metals. Advantageously, chemical reagents are used to reduce the formation of anionic species, such as hydroxide ($OH^-$) or oxide ($O^{-2}$) ions, in the matrix that precipitate metals. Metal-complexing reagents, for example organic acids including formic acid, acetic acid, and glycolic acid, are injected into carrier solutions to simultaneously perform two functions: 1) organic acids are weakly ionized and can pass through the membrane easily and form stable complexes with trace metals; and 2) organic acids maintain a lower pH inside the sample channel to reduce metal precipitation. These metal complexes are stable enough to keep the metals in solution but also sufficiently ionizable to breakdown in an analytical instrument, such as an electrospray mass-spectrometer (ES-MS), for analysis.

In accordance with the present invention, depending on the nature of the matrix, different ratios, combinations, and concentrations of organic and inorganic reagents are included in carrier solution to neutralize, modify, and/or eliminate the matrix of a solution sample while simultaneously stabilizing trace metals in solution. In one example, with no intent to limit the invention thereby, applicable organic and inorganic reagents include formic acid, acetic acid, oxalic acid, glycolic acid, ethylenediaminetetraacetic acid (EDTA), nitrotriacetic acid (NTA), diethylenetriaminepentaacetic acid (DTPA), ethylenediamine (EDA), glycine, iminodiacetic acid (IDA), and amines. Advantageously, the present invention allows for accurate and substantially real-time analysis of trace metals and speciation of the metals.

FIG. 1 shows a block diagram illustrating an apparatus 100 for analyzing trace metals in accordance with one embodiment of the present invention. A sample is extracted from a process wet bath (not shown) by a sampling apparatus 102, which can include a variable speed syringe in one example.

In one embodiment of the present invention, the solution sample is extracted after the sample solution has been mixed with appropriate isotope mixtures, which can be used to achieve calibration-free mass spectrometry measurements as disclosed in U.S. Pat. No. 5,414,259, issued May 9, 1995 to Kingston. Generally speaking, assuming that an analysis for metal content is required, one takes a sample of the solution to be analyzed, spikes the sample with an enriched standard solution having a substantially different isotope ratio than the naturally-occurring ratio, introduces the spiked sample to a mass spectrometer, and records the measured mass ratio between the isotopes. The measurement is going to differ from the naturally-occurring ratio and the standard spike ratio, and based upon the measured ratio, the known quantity of the original sample, and the known quantity of the added spike solution, one can calculate the single unknown, that being the concentration of the metal in the original sample. In other embodiments, the sample is extracted without an isotope spike and the matrix of the sample is eliminated, neutralized, and/or modified in accordance with the present invention.

Referring again to FIG. 1, the extracted sample is pushed by sampling apparatus 102 into mixing tee 104, then drawn through valve stack 106 including valves 106A, 106B, 106C, and 106D, and loaded into variable speed syringe 108.

Valve 106C is then positioned to allow syringe 108 to push the sample through line 109 and into sample input port 110 of electrodialysis apparatus 112. The sample then flows through a sample channel 113 of electrodialysis apparatus 112 and exits sample channel 113 through sample output port 114.

The matrix-treated sample is then transported through lines 115, 117, and 119, passing through valve 116A and fluid sensor 118 prior to entering sample reservoir 120 for temporary storage. After all of the initially drawn sample is treated, valve 116A is positioned to transport the treated sample in reservoir 120 back past fluid sensor 118, through valve 116A and through valve 116B via line 121. The treated sample is then drawn through line 123, valve 106B, valve 106C, and valve 106D into syringe 108.

Finally, valve 106D is positioned to allow syringe 108 to push the treated sample through line 129, through valve 106D, and through line 131 to an analyzer apparatus 132, which can detect trace contaminants in the sample.

Fluid sensor 118 is used to determine any change in the sample volume and resultant change in the required stroke on syringe 108 when drawing treated sample back to itself. Fluid sensor 118 controls the movement of syringe 108 and based upon the position of syringe 108, calculates the volume of the sample being treated. Once a certain amount of sample is detected or calculated by fluid sensor 118 as having been treated and stored in reservoir 120, the partially-treated sample is pulled back into syringe 108 from reservoir 120 as noted above. The flow of sample from syringe 108 to reservoir 120 and back to syringe 108 constitutes one cycle. In one example, with no intent to limit the invention thereby, fluid sensor 118 is a digital fiber sensor, part number FX-301-F, available from Powermatic Associates of Pleasanton, Calif.

Whenever electrodialysis apparatus 112 is in use, carrier solution is sent through electrodialysis apparatus 112, specifically through carrier solution channels, to treat the sample flowing through a sample channel of electrodialysis apparatus 112.

Carrier solution reservoir 134 is filled with concentrated carrier solution reagent and pressurized with ultra pure nitrogen to approximately 5 psi. A variable speed syringe 138 is filled with concentrated carrier solution reagent from carrier solution reservoir 134 by drawing the reagent through line 135, valve 136A, and line 137. Variable speed syringe 138 is computer controlled to empty at a rate to achieve an appropriate final carrier solution concentration, passing concentrated reagent through valve 136B, line 139, check valve 140, line 141, and into mixing tee 142, where the concentrated reagent is mixed with pressure regulated ultra pure water (UPW).

The carrier solution including water and reagent is then sent through line 143 and micro-metering valve 144, which sets the flow rate of the carrier solution. Shut-off valve 146 is used to stop the flow of carrier solution when electrodialysis apparatus 112 is not in use. The carrier solution then flows through line 147 and into a carrier solution input port 148 of electrodialysis apparatus 112, through carrier solution channels 149A and 149B, and exits through a carrier solution output port 150. A line 151 transports the spent carrier solution to a drain 152 for disposal.

In one example, with no intent to limit the invention thereby, variable speed syringes 108 and 138 are computer controlled and include a stepper motor controlled syringe with a KEL-F piston, Teflon syringe barrel, and fluorocarbon seals.

In one example, with no intent to limit the invention thereby, valve stack 106 including valves 106A, 106B, 106C, and 106D, is made up of valves having part number CASY-1427-03, available from Bay Advanced Technology of Menlo Park, Calif.

In one example, with no intent to limit the invention thereby, three-way valves 116A and 116B, are valves having part number PV-1-2312, also available from Bay Advanced Technology of Menlo Park, Calif.

In one example, with no intent to limit the invention thereby, valves 119A and 119B are valves having part number AMGZ0-6BUS-2, and valve 123 is a valve having part number AMGZ1-6BUS-2, all available from CKD of Rolling Meadows, Ill.

Carrier solution reservoir 134 is a vessel compatible with acidic solutions and in one example, is capable of being pressurized to 5 psi.

In one example, with no intent to limit the invention thereby, mixing tees 104 and 142 are made of Kel-F and Y-shaped to provide sufficient mixing of input solutions without leaching of contaminants. However, various mixing tees are applicable such as those that provide sufficient mixing, cleanliness, and compatibility with various solutions.

In one example, with no intent to limit the invention thereby, metering valve 144 is a valve having part number P-445, and check valve 146 is a valve having part number CV-3000, both available from Upchurch Scientific of Oak Harbor, Wash.

In one example, with no intent to limit the invention thereby, vented reservoir 120 is also made of Kel-F to provide compatibility with various solutions without leaching of contaminants. However, various reservoirs are applicable such as those that provide storage ability with sufficient venting capability, compatibility with various solutions, and cleanliness.

In one example, with no intent to limit the invention thereby, electrodialysis apparatus 112 may be an apparatus having part number P-N053948, available from Dionex Corporation of Sunnyvale, Calif. However, various applicable electrodialysis apparatus may be used as will be apparent to those of ordinary skill in the art.

It is noted that lines transporting sample solution or carrier solution may comprise piping, fittings, and/or tubing in one example, but any applicable material and structure that allows for the accurate transfer of liquids may be used to operably connect to valves, syringes, reservoirs, and other apparatus in accordance with the present invention. In one example, with no intent to limit the invention thereby, components are connected with tubing made of Teflon® PFA 450 HP fluoropolymer, having 0.062" O.D.×0.016" I.D., Part #106-0062016, available from Parker Hannifin of Cleveland, Ohio.

Figure 2:
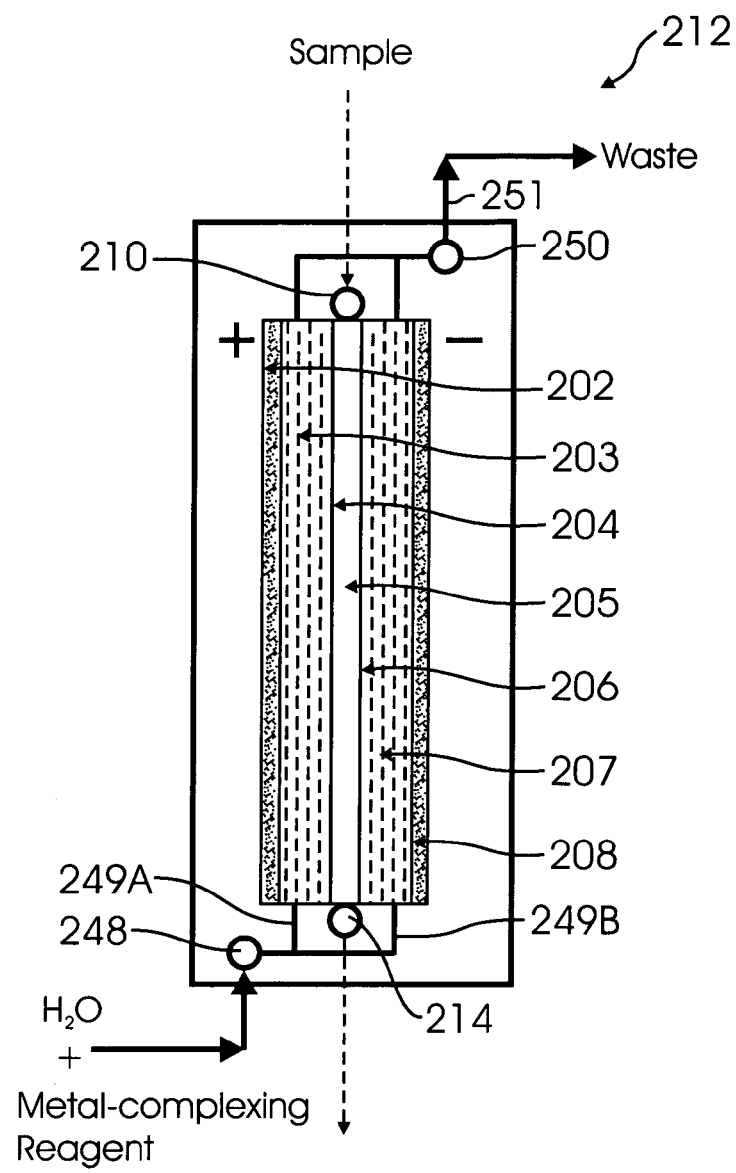
FIG. 2 is an illustration of an electrodialysis apparatus, in accordance with an embodiment of the present invention.

Referring now to FIG. 2, an illustration of an electrodialysis apparatus 212 and flow paths of a solution sample and carrier solution are shown in accordance with one embodiment of the present invention. Electrodialysis apparatus 212 is an embodiment of electrodialysis apparatus 112 shown in FIG. 1. In one example, with no intent to limit the invention thereby, electrodialysis apparatus 212 is a "Self-Regenerating Suppressor" (SRS) having part number P-N053948, available from Dionex Corporation of Sunnyvale, Calif., and described in U.S. Pat. Nos. 4,999,098, 5,518,522, and 5,597,481, which are incorporated by reference herein for all purposes.

As shown in FIG. 2, electrodialysis apparatus 212 includes three solution channels: a middle sample channel 205 defined by ion-exchange membranes 204 and 206; and two carrier solution channels 203 and 207 sandwiching sample channel 205. Carrier solution channels 203 and 207 are defined by membrane 204 and anode electrode 202, and membrane 206 and cathode electrode 208, respectively. Carrier solution channels 203 and 207 can also be defined by a membrane and other layers coupled to the interior surface of an electrode (i.e., surface closest to the membrane) that allow carrier solution to come into contact with the electrode, for example gasket structures with screens and/or holes.

A solution sample enters electrodialysis apparatus 212 through a sample input port 210. The sample then flows through sample channel 205 and exits sample channel 205 through sample output port 214. The carrier solution enters electrodialysis apparatus 212 through a carrier solution input port 248 and flows through carrier solution channels 203 and 207. After passing through channels 203 and 207, the spent carrier solution exits electrodialysis apparatus 212 through carrier solution output port 250, passes through a line 251, and is transported to a drain 152 (FIG. 1) for eventual disposal.

The same carrier solution enters electrodialysis apparatus 112 through one inlet and is then separated into split streams 249a and 249b, one stream to flow through channel 203 and the other stream to flow through channel 207. Accordingly, the flow rate, concentration, and makeup of carrier solution is the same on both sides of sample channel 205 in this embodiment.

Other devices having different membrane, sample channel, and/or carrier solution channel configurations may be used. In accordance with another embodiment of the present invention, an electrodialysis apparatus 312 and flow paths of a solution sample and carrier solution are shown in FIGS. 3A through 3C.

Figure 3A:
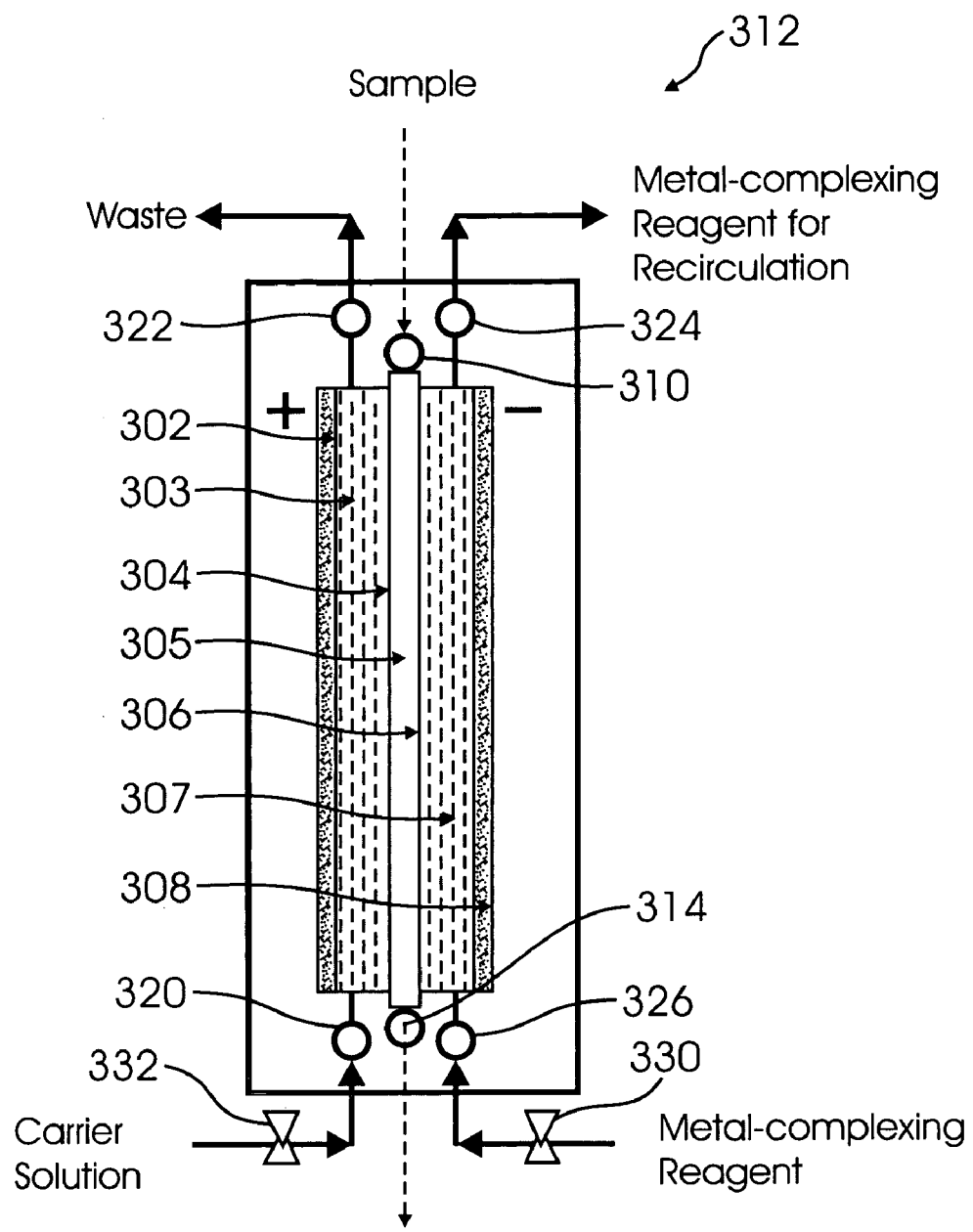
FIGS. 3A–3C are different views of another electrodialysis apparatus, in accordance with another embodiment of the present invention.
Figure 3B:
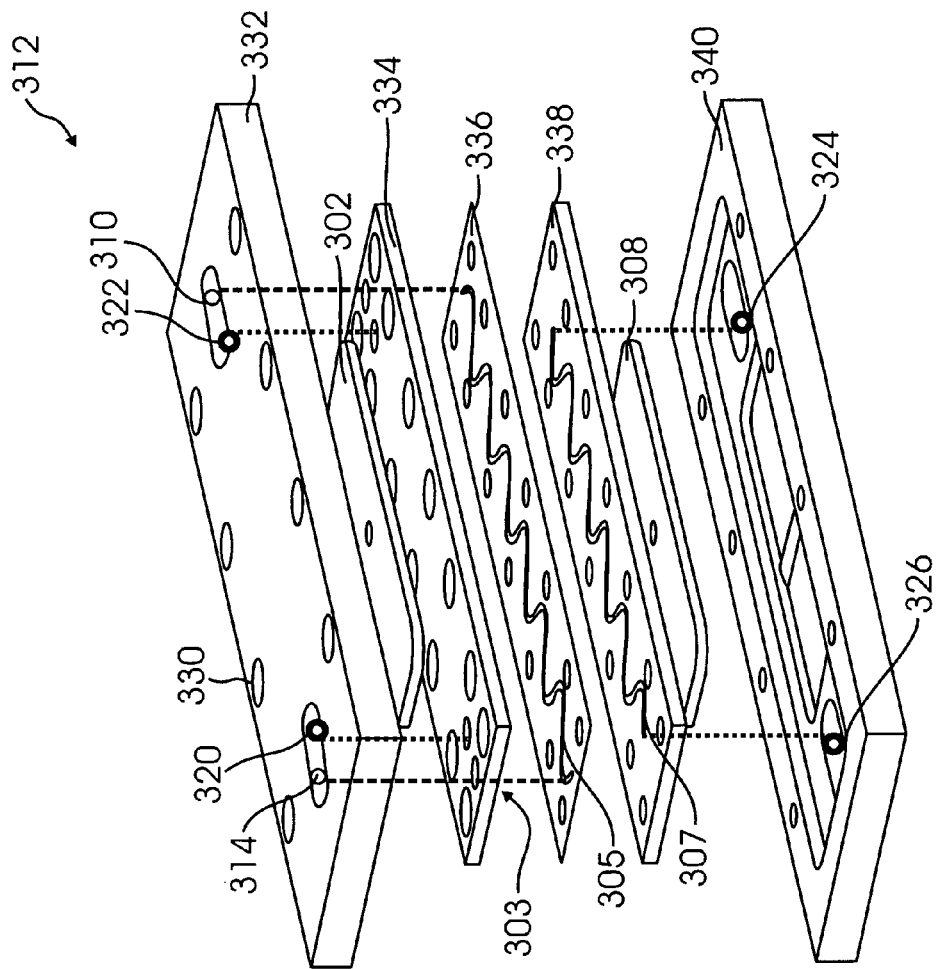
Figure 3C:
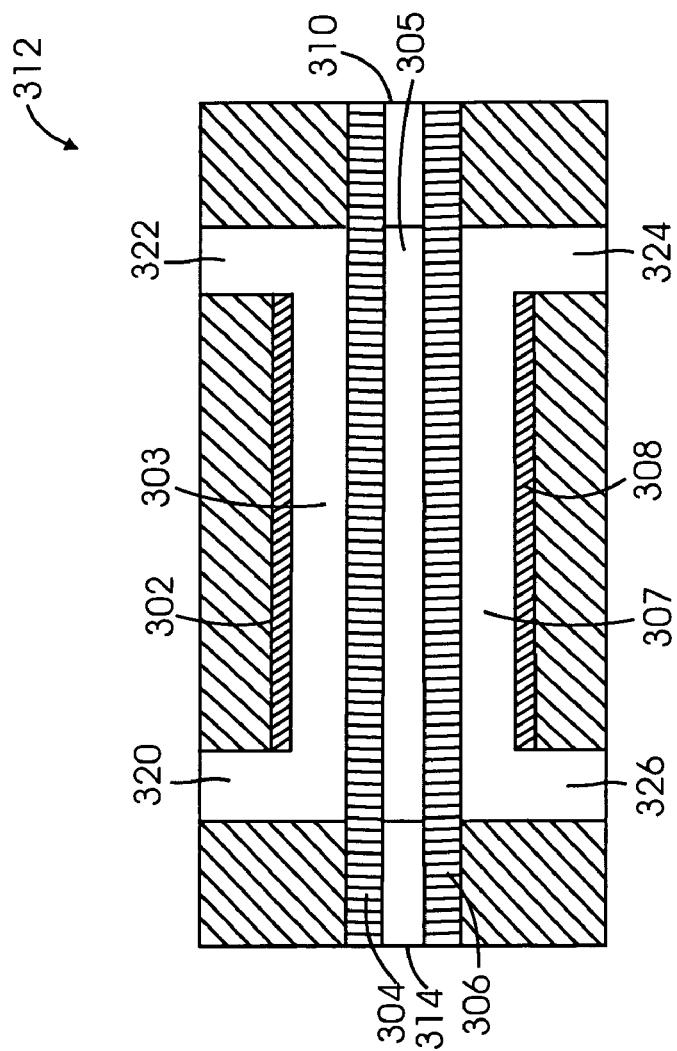

As shown in FIGS. 3A through 3C, electrodialysis apparatus 312 also includes three solution channels: a middle sample channel 305 defined by ion-exchange membranes 304 and 306; and two carrier solution channels 303 and 307 sandwiching sample channel 305. Carrier solution channels 303 and 307 are defined by membrane 304 and anode electrode 302, and membrane 306 and cathode electrode 308, respectively. Carrier solution channels 303 and 307 can also be defined by a membrane and other layers coupled to the interior surface of an electrode (i.e., surface closest to the membrane) that allow carrier solution to come into contact with the electrode, for example gasket structures with screens and/or holes.

A solution sample enters electrodialysis apparatus 312 through a sample input port 310. The sample then flows through sample channel 305 and exits sample channel 305 through sample output port 314. The carrier solution enters electrodialysis apparatus 312 through separate carrier solution input ports 320 and 326. The carrier solution streams then flow through carrier solution channels 303 and 307, and exits through separate carrier solution output ports 322 and 324.

In this embodiment, carrier solution is fed into carrier solution channels 303 and 307 through separate carrier solution input ports 320 and 326 such that channels 303 and 307 can be operated individually. Advantageously, individual control over the carrier solution channels allows for increased flexibility in treating the sample matrix as will be explained in greater detail below.

In one embodiment, two different kinds of carrier solution may be used at the same time to treat the sample matrix. For example, when treating a sulfuric acid matrix, only ultra pure water (UPW) is used as carrier solution in channel 303 while formic acid, acting as a metal-complexing reagent, is used in channel 307. In another example, a very dilute solution of barium hydroxide (BaOH) is used as carrier solution in channel 303 and formic acid is used in channel 307. In channel 303, barium ($Ba^{2+}$) ions react with sulfate ($SO_4^{2-}$) ions from the sample matrix and form very stable barium sulfate ($BaSO_4$) precipitates that are carried away to waste via channel 303. In the second example, the neutralization of $H_2SO_4$ occurs much faster as compared to using only UPW as a carrier solution in the first example.

It is also desirable at times to have control over the flow rate of the carrier solution flowing through each carrier solution channel. For example, in the beginning of sample matrix neutralization, when the concentration of a matrix is very high, the flow rate of carrier solution including metal-complexing reagent in channel 307 can be slowed, thereby allowing for transfer of more reagent to the sample channel. In another example, increasing the flow rate of water in channel 303 helps to carry away more matrix ions, thereby neutralizing, eliminating, and/or modifying the matrix more quickly.

Depending on the nature of the matrix, it is also desirable at times to change the concentration of the same carrier solution in the carrier solution channels. For example, during the initial treatment of the solution sample, the initial concentration of metal-complexing reagent may be made higher in the carrier solution charged by the cathode electrode to help stabilize the metals in the sample earlier in time when there is a greater chance of metal precipitation, for example with hydroxide. A reagent in the carrier solution channel charged by the anode electrode may undergo oxidation reactions and is therefore less effective in treating the sample matrix. By mixing the same concentrated reagent solution with different proportions of water, it is possible to control the concentration of reagents in the carrier solution channels.

Another advantage of having two independent channels is that in channel 307 charged by cathode electrode 308, the metal-complexing reagent, such as carboxylic acid, does not undergo any chemical change. Thus, the reagent is very clean and can be recirculated or used in another electrodialysis apparatus if multiple electrodialysis apparatus are used in series. If the metal-complexing reagent is recirculated, the cost of operation will be reduced and in many cases so will the cost of waste disposal.

Referring now to FIG. 3B, a perspective assembly view of electrodialysis apparatus 312 is illustrated in accordance with one embodiment of the present invention. A central plate 336 includes sample channel 305 cut through plate 336. Central plate 336 is formed of a chemically-inert and non-contaminating material and in one example, plate 336 is formed from a material including Teflon. In this embodiment, sample channel 305 is cut into a winding snake-like path but may be cut into various shapes as is apparent to those of ordinary skill in the art.

Membranes (not shown) are placed on both sides of plate 336 to define sample channel 305 between the membranes and the cut path through central plate 336. Blocks 334 and 338 are then placed over a corresponding membrane. Blocks 334 and 338 are formed of a chemically-inert and non-contaminating material and in one example, blocks 334 and 338 are formed from a material including Teflon. Carrier solution channel 303 is cut into block 334 to exactly correspond to the path of sample channel 305. Carrier solution channel 307 is cut into block 338 to also exactly correspond to the path of sample channel 305. Electrodes 302 and 308 are operably coupled to block 334 and 338, respectively, such that the electrodes are in contact with carrier solution that flows through the respective carrier solution channels.

Outer cover members 332 and 340 house the electrodes, membranes, carrier solution channel blocks, and the central plate. Outer cover members 332 and 340 are formed from material resistant to wear and in one example, members 332 and 340 are formed from material including polypropylene. Sample input port 310 and sample output port 314 are shown on cover member 332. Carrier solution input port 320 and carrier solution output port 322 are also shown on cover member 332. Carrier solution input port 326 and carrier solution output port 324 are shown on cover 324. However, it should be apparent that other configurations of the membrane, sample channel, carrier solution channel, solution input ports, and/or solution output ports is within the scope of the present invention.

Other apertures on cover members 332, electrodes 302 and 308, central plate 336, and blocks 334 and 338 are used to operably couple the parts of the apparatus together and, in one example, holes 330 are apertures for receiving screws or rods.

FIG. 3C shows electrodialysis apparatus 312 in cross section with sample channel 305 bound by membranes 304 and 306. Carrier solution channels 303 and 307 are defined by electrode 302 and membrane 304, and membrane 306 and electrode 308, respectively.

Depending on the nature of the sample matrix, the ion-exchange membrane is selected. For example, in the case of acidic matrixes, a cation ion-exchange membrane (e.g., Dionex Corp.'s "Cation SRS", Part No. 053948) is used, while for basic matrixes, an anion ion-exchange membrane is used (e.g., Dionex Corp.'s "Anion SRS", Part No. 053946).

In one embodiment, membranes 304 and 306 may be identical, but need not be necessarily the same. For added flexibility, membranes 304 and 306 may be different membranes and/or include different functional exchange groups with different backbone to allow for selective control over passage through the membrane based upon ion-type and/or chemical group. In one example, with no intent to limit the invention thereby, membrane 304 adjacent the anode may be a Neosepta AMX ion-exchange membrane with a polystyrene based backbone, available from Tokuyama Soda Co. Ltd., of Japan. In this example, membrane 304 is strongly basic anion permeable that is resistant at lower pH. In a further example, with no intent to limit the invention thereby, membrane 306 adjacent the cathode may be a Neosepta AHA anion-exchange membrane with polyethylene based backbone that is resistant at high pH, also available from Tokuyama Soda Co. Ltd., of Japan.

Figure 4A:
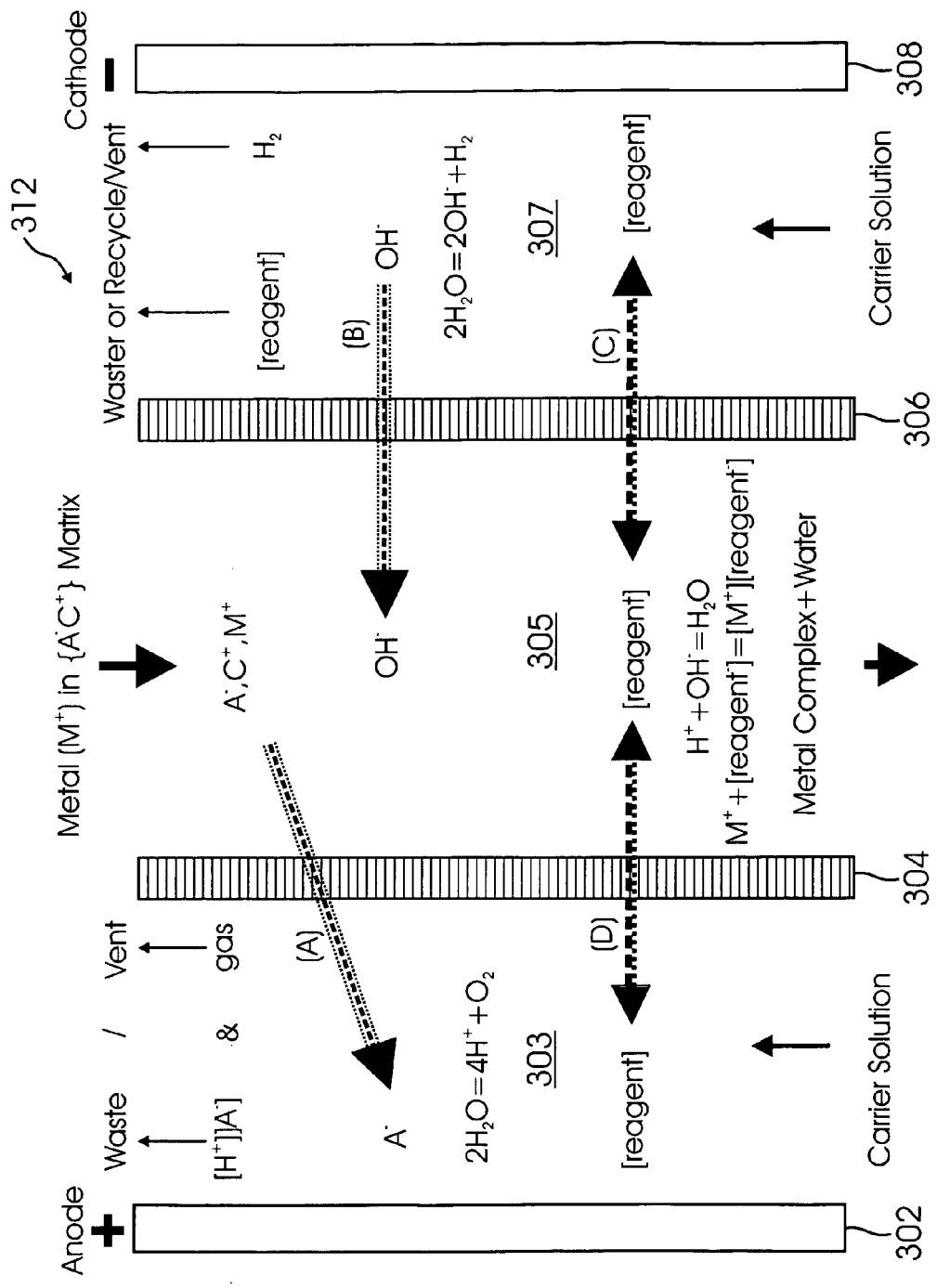
FIGS. 4A and 4B are illustrative diagrams of the flow path and chemistry of the solution sample and carrier solution as the solutions flow through an electrodialysis apparatus, in accordance with an embodiment of the present invention.

Referring now to FIG. 4A, the chemistry of the solution sample and carrier solution when flowing through electrodialysis apparatus 312 is illustrated, in accordance with one embodiment of the present invention. When an electrical potential is applied across electrodes 302 and 308, the ions in the sample matrix are attracted towards its opposite charge resulting in an increase in mobility of the ions of interest across the membranes. For example anions $A^-$ in the matrix are attracted towards anode (+ve) electrode 302 and cations $C^+$ are attracted towards cathode (-ve) electrode 308.

The movement of anions or cations can be controlled by placing appropriate ion-exchange membranes 304 and 306 between sample channel 305 and carrier solution channels 303 and 307, respectively. For example, when sample channel 305 and carrier solution channels 303 and 307 are separated by an anion exchange membrane, the positive charge on the membrane will allow only anions, negatively charged ions, to pass toward positively charged anode electrode while cations, positively charged ions, will be retained inside sample channel 305. By the law of electroneutrality, total charge should be maintained on both sides of the membrane. To satisfy this law, small anions will diffuse through the membrane from the cathode side in this example.

During continuous sample matrix neutralization, elimination, and/or modification, it is desirable to keep the electrodes efficient at all times. To achieve electrode efficiency, fresh streams of carrier solution are moved through carrier solution channels 303 and 307 and onto the surface of the electrodes. A constant DC current is applied to the electrodes and actual current and voltage feedback can be monitored by computer. The efficiency of neutralization, elimination, and/or modification depends on the sample flow rate, surface area of the membrane that comes in contact with the sample, concentration and nature of the anions, and current applied. These parameters are specific for each sample matrix.

Carrier solution plays an important part in the elimination and electro-neutralization of ionic charge within the sample matrix. The selection of carrier solution is also very important as the nature and concentration of carrier solution will determine not only the success of matrix neutralization or elimination but also metal stabilization.

For example, if an acidic matrix, such as sulfuric acid ($H_2SO_4$), is required to be neutralized and only ultra pure water is used as carrier solution, carrier solution channel 303 charged by anode electrode 302 will carry away anions (e.g., $SO_4^{2-}$) from the sample matrix in sample channel 305 to drain 152 (FIG. 1). However, carrier solution channel 307 charged by cathode electrode 308 will produce negatively charged hydroxide ($OH^-$) ions that pass through membrane 306 to balance the charge inside sample channel 305 and then react with the cation components of the sample matrix, metals in one example ($M^+$), which will form salts (MOH) that may precipitate on the membrane, not allowing for or greatly hindering subsequent trace metal analysis.

In accordance with an embodiment of the present invention, metal-complexing reagents are used in the carrier solution to treat the sample solution allowing for subsequent detection of trace contaminants including metals.

Referring again to FIG. 4A, the carrier solution, including a metal-complexing reagent ([reagent]) and water ($H_2O$), is electrolyzed at the surface of two (anode and cathode) electrodes 302 and 308, preferably comprised of platinum. At the cathode surface, water is electrolyzed into hydrogen ions ($H^+$) and hydroxide ions ($OH^-$). The hydrogen ions reduce, accepting two electrons, and are converted into hydrogen gas ($H_2$). On the other side, at the anode surface, the carrier solution is oxidized into hydrogen ions and oxygen or carbon dioxide gas, depending on the nature of reagent used in the carrier solution. In one example, when carboxylic acid is used as the metal-complexing reagent, carbon dioxide gas is evolved at the anode.

During a neutralization process, under the influence of a potential gradient created by the electrodes, anions $A^-$ of the sample matrix pass through membrane 304 toward anode electrode 302 and into carrier solution channel 303, as shown by dashed arrow (A). The neutral species of weakly-ionized reagent permeate freely through the membranes and into sample channel 305, as shown by dashed arrows (C) and (D). To keep the electro-neutrality balance inside sample channel 305, hydroxide ions ($OH^-$) from carrier solution channel 307 pass into sample channel 305, as shown by dashed arrow (B), where the hydroxide ions deprotonate non-ionized reagent, undergoing an acid-base reaction, and produces water and active anionic complexing ligands ([reagent$^-$]). The anionic ligands form complexes with cationic metals and stabilize them in solution.

Figure 4B:
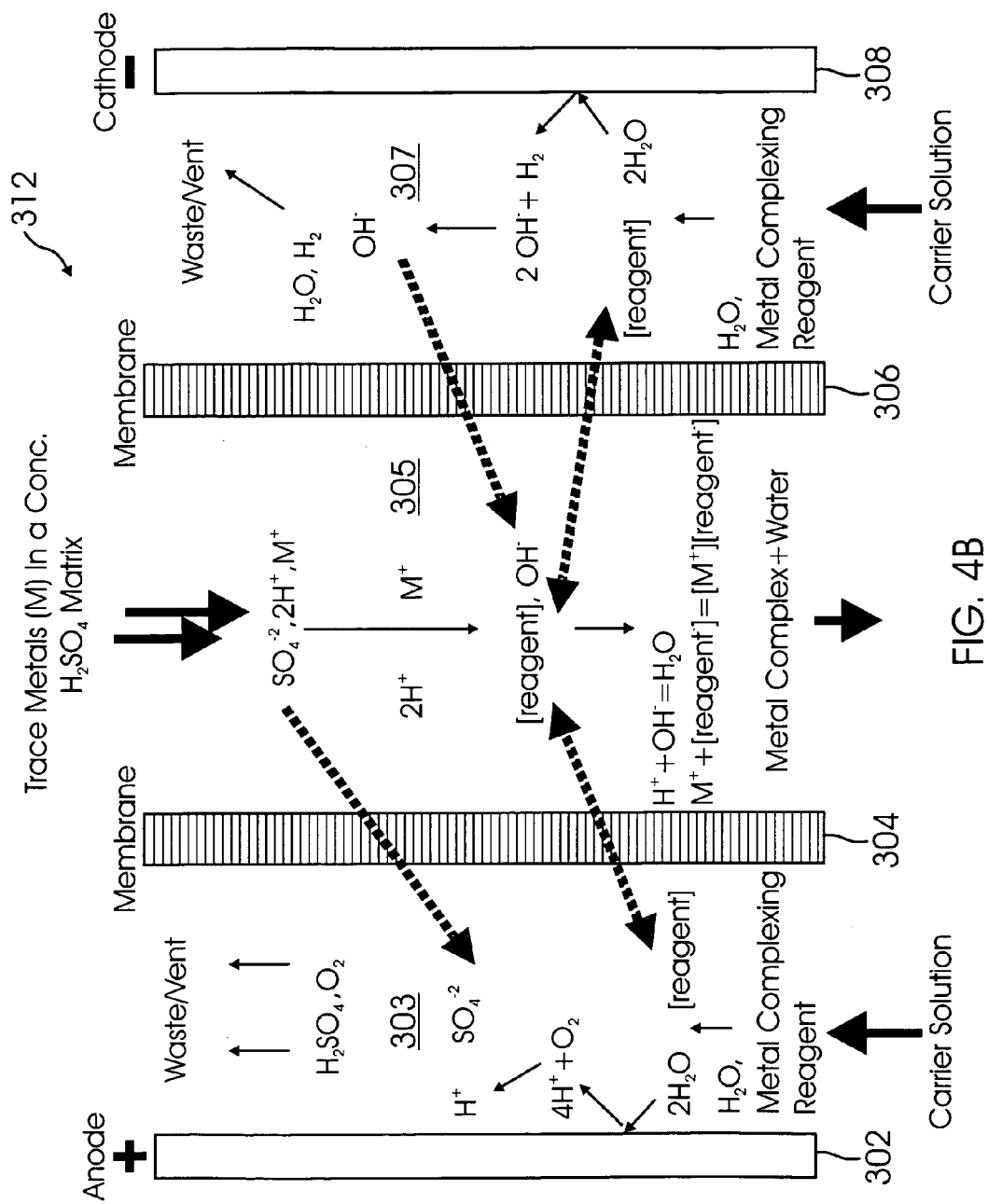

Referring now to FIG. 4B, an example of treatment of a sulfuric acid matrix is shown in accordance with the present invention. A solution sample includes trace metals in a concentrated sulfuric acid ($H_2SO_4$) matrix. The sulfuric acid dissociates into anions and cations by the following equation:

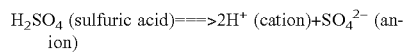

As the anion part of the sample solution passes through membrane 304, negative charge inside sample channel 305 is depleted. To balance the charge, anions from the carrier solution along with neutral undissociated species of the metal-complexing reagent enter sample channel 305 from carrier solution channel 307 charged by cathode electrode 308. For example, in which formic acid is the reagent:

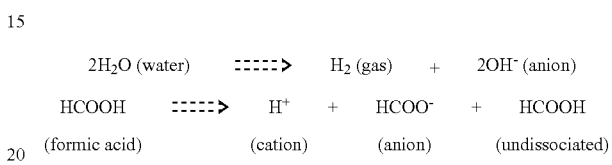

In a further example, the contamination level of copper metal ($Cu^{2+}$) and its speciation in a sulfuric acid ($H_2SO_4$) matrix is determined by using an electro-spray mass spectrometer (ES-MS) after sample treatment by electrodialysis. Glycolic acid is used as the reagent dissolved in water to form the carrier solution used to neutralize the sulfuric acid ($H_2SO_4$) matrix and to stabilize $Cu^{2+}$ in the sample solution. Since $H_2SO_4$ is a strong acid, $H_2SO_4$ fully dissociates in solution into hydrogen ions ($2H^+$) and sulfate ions ($SO_4^{2-}$) in sample channel 305. Glycolic acid is a weak acid resulting in many undissociated molecules in solution in carrier solution channels 303 and 307. During electrolysis, at the anode surface, the glycolic acid is oxidized into glyoxylic acid and then to oxalic acid that is further oxidized into carbon dioxide gas. At the cathode surface, water is electrolyzed into hydrogen gas ($H_2$) and hydroxide ions ($OH^-$). The following sets forth the aforementioned chemical reactions in chemical equation form:

In the Anode Carrier Solution Channel:

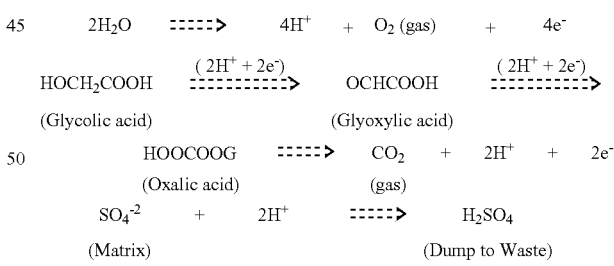

In the Cathode Carrier Solution Channel:

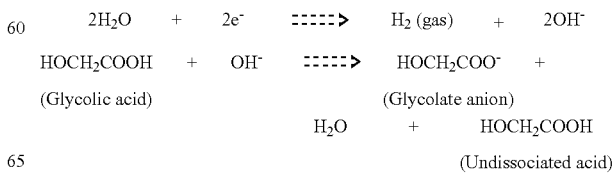

In the Sample Channel:

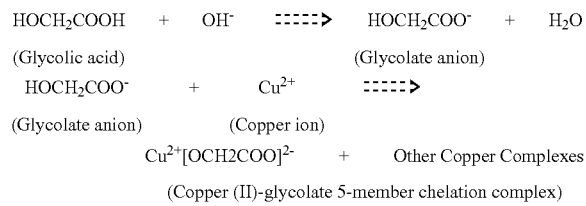

The stabilities of metals in solution are a key component to success of subsequent analysis for detecting trace metals. Most metals are usually stable in solution either at low pH, when it does not form insoluble hydroxide ($OH^-$) or oxide ($O^{-2}$) salts, or if some kind of coordination complex is formed with chemical ligands. Generally, there are two kinds of groups or classes that form coordinate bonds between ligands and metals: 1) primary acid groups in which the hydrogen ion is replaced with a metal ion; and 2) neutral groups which contain an atom with a free electron pair suitable for bond formation. If two groups from either Class 1 or 2 from both classes, are present in the same molecule in such position that both groups can form bonds with the same metals ion, a chelate ring may be formed. This chelation ring stabilizes the metals in solution.

An example of a Class 1 member is formic acid (HCOOH), where the metal ion ($M^+$) combines with the formate ion ($HCOO^-$) to form metal-formate (HCOOM).

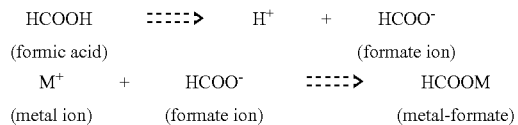

In yet another example of a Class 1 member, acetic acid forms a 4-member chelate ring with polyvalent metals like Copper(II)-acetate, as illustrated below.

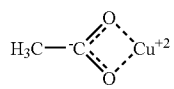

An example of a Class 2 member is glycolic acid ($HOCH_2COOH$), which uses both the hydroxyl ($OH^-$) and carboxylic ($COOH^-$) groups to form five-member chelation complexes with polyvalent metals like copper, zinc, and nickel. This metal ion complexing ability is useful to obtain stability of metals in solution.

In many cases, when a solution matrix is highly concentrated (e.g., highly acidic or basic), it takes a very long time at a very slow flow rate of sample to pass through the electrodialysis apparatus before desired volumes of the sample matrix is fully neutralized, modified, and/or eliminated. To overcome this problem, the present invention provides for an increased sample flowrate through the sample channel, collection of the treated sample in a heated reservoir, and re-flow of the treated sample through the sample channel with reverse polarity of the electrodes to advantageously increase sample throughput.

For example, fully neutralizing 1800 µL of 24% $H_2SO_4$ will take about 36 minutes with a single pass but in accordance with the method and apparatus of the present invention, the same volume and concentration of $H_2SO_4$ will take only about 8 minutes if recirculated four times with reverse polarity.

Figure 5:
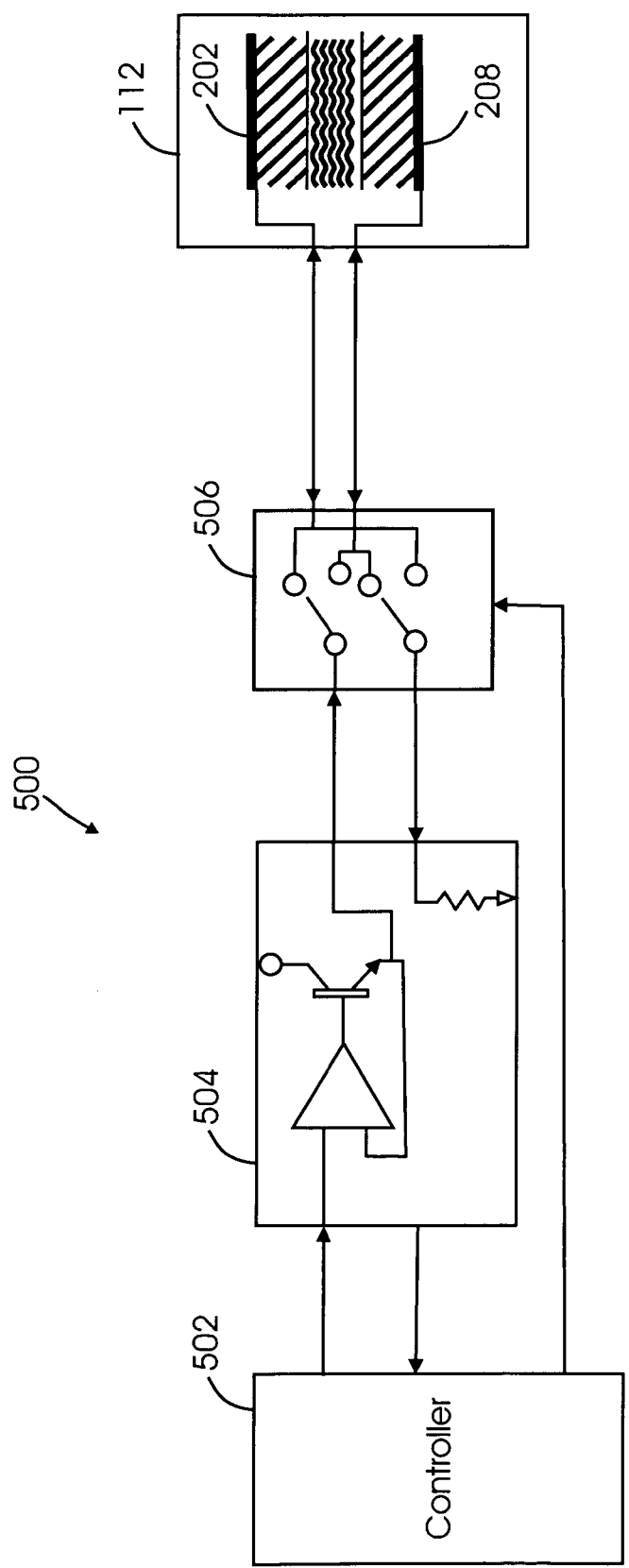
FIG. 5 is a block diagram of an electric power supply and reverse polarity switch with control system, in accordance with an embodiment of the present invention.

FIG. 5 illustrates a block diagram of a polarity switching system 500 including an electric power supply 504, reverse polarity switch 506, and controller 502 that can be used in accordance with an embodiment of the present invention.

A microprocessor-based controller 502, with either discrete or serial communication, and analog or digital control, applies an operator-selected current setpoint to a current regulated power supply 504. Actual current and voltage feedback may be monitored by controller 502 for diagnostic purposes. The desired current is set by controller 502 to achieve optimum neutralization rate. In one example, with no intent to limit the invention thereby, controller 502 includes a Contec PR105 Chassis, ACE 870 Power Supply, IP5S2 Passive Backplane, PCISA-3716 Single Board Computer, plus Measurement Computing DAS1002, available from Automation and Control Products of San Jose, Calif.

Current regulated power supply 504 provides either regulated DC or PW controlled DC average current to polarity switching relay 506. In one example, with no intent to limit the invention thereby, power supply 504 is a model PWR-2A available from Merobel of France.

Polarity switching relay 506 receives current from current regulated power supply 504 and switches direction of current supplied to electrodes 202, 208 of electrodialysis apparatus 112 at the command of microprocessor controller 502. In one example, with no intent to limit the invention thereby, polarity switching relay 506 is a model RH2B-UL available from IDEC Corporation of Japan. In order to maximize the lifetime of the membrane hardware, the current can be reversed periodically.

As previously noted, reservoir 120 (FIG. 1) is preferably heated in accordance with one embodiment of the present invention because heat increases the diffusion rate across the membrane upon re-flow of the sample through the sample channel and also re-dissolves any crystal that may have formed back into solution. Thus, having reservoir 120 heated reduces the time required for neutralization but does not affect the characteristics of the matrix.

Figure 6:
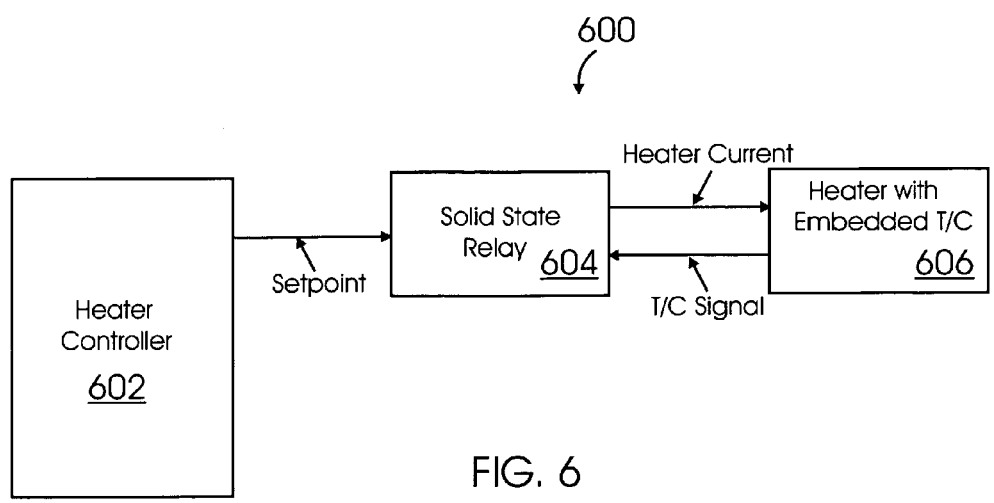
FIG. 6 is a block diagram of a sample reservoir heater assembly with control system, in accordance with an embodiment of the present invention.

FIG. 6 shows a block diagram of a sample reservoir heater system 600 in accordance with an embodiment of the present invention.

Heater controller 602 is a small, commercially available, PID based micro controller with local operator setpoint. It reads heater temperature via thermocouple (T/C) input and can display actual temperature on the front panel display. The output is standard PWM for temperature regulation.

Solid state relay 604 converts the PWM output signal from heater controller 602 and switches 24 VDC for controlling heater current.

Heater 606 is fabricated from nichrome resistive heating elements with embedded Type J thermocouples. The reservoir is kept between about 70° C. and about 90° C. in one example.

Figure 7:
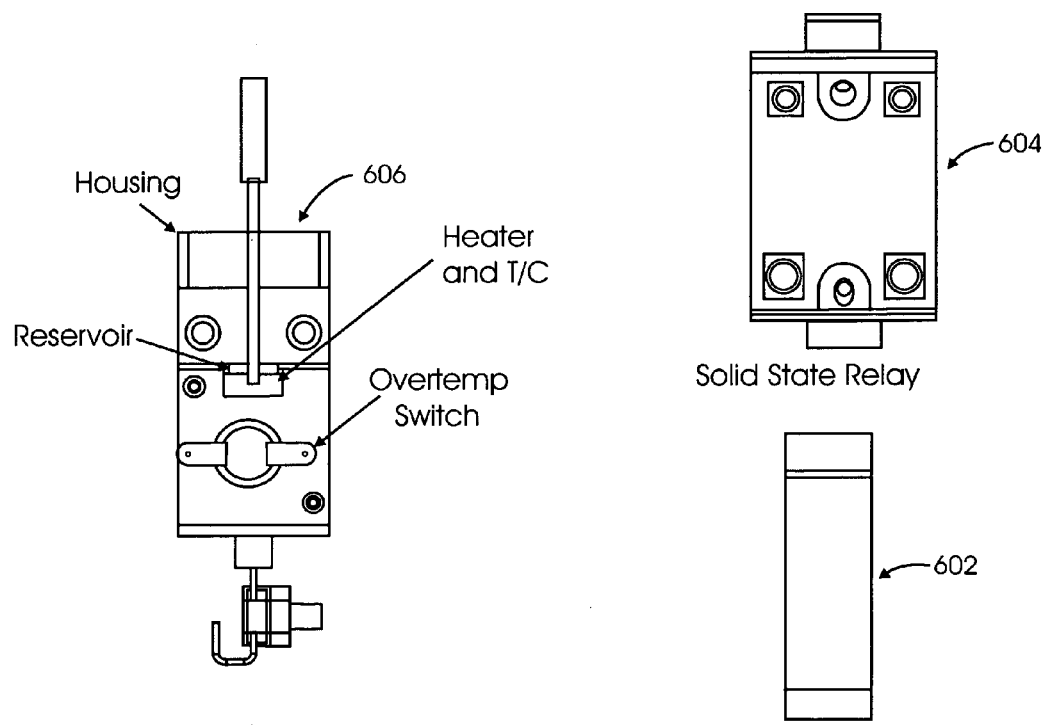
FIG. 7 is an illustration of a sample reservoir heater assembly, in accordance with an embodiment of the present invention.

FIG. 7 illustrates a sample reservoir heater system including a heater controller 602, solid state relay 604, and heater 606, in accordance with an embodiment of the present invention.

The method and apparatus of the present invention can be utilized as a stand alone module or can be incorporated with sampling and analytical instruments. In one example, the electrodialysis apparatus and method of the present invention is integrated with a "Trace Contamination Analyzer" (TCA) or a "Chemical Constituents Analyzer" (CCA), both available from Metara Inc. of Sunnyvale, Calif. Advantageously, in one embodiment, all operations starting from sample extraction to analysis are on-line, automated, and controlled by computer.

The whole operation, to extract the sample, mix the predetermined spike and to neutralize the matrix by membrane is on-line automated and controlled by computer. In the beginning of the process, a "job" is built by selecting the type of matrix being investigated, for example UPW, HF, or $H_2SO_4$. Then the variable parameters such as the sample volume, neutralization speed, neutralization cycles, current and polarity are selected using an electrodialysis apparatus configuration file such as that shown in FIG. 8.

In one example, as shown in FIG. 8, the membrane configuration file is an ASCII text file, editable in any text editor, which contains configuration parameters that instruct software how to operate the hardware. The solution matrix is the primary criteria. In one example, the software is entitled "Job Scheduler" available from Metara, Inc. of Sunnyvale, Calif. The file is read and parsed by the Metara Job Scheduler with C++ classes (Microsoft® CString and CFile classes).

Figure 9:
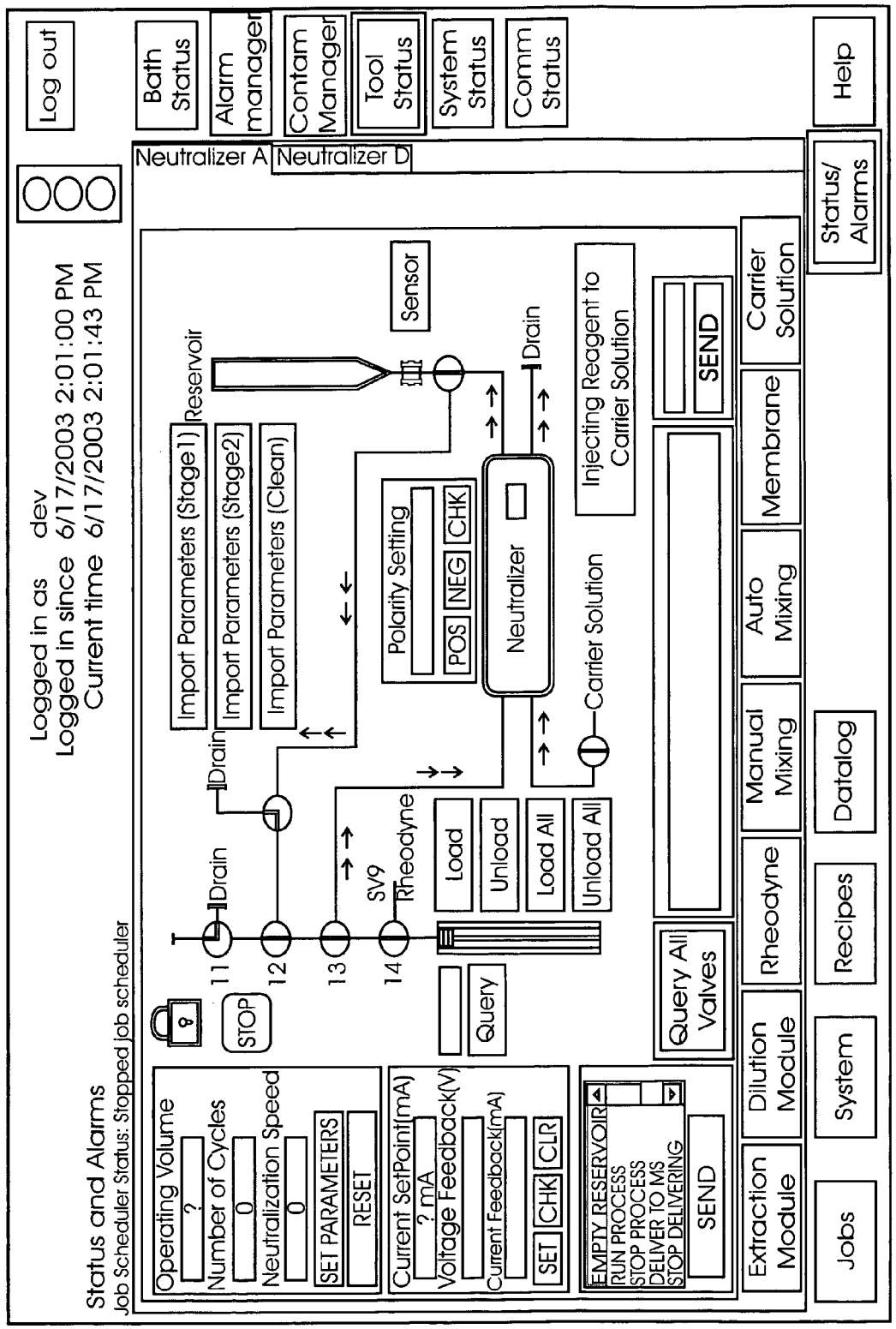
FIG. 9 is a screen shot from a computer controlling the apparatus for analyzing trace metals, in accordance with an embodiment of the present invention.

FIG. 9 shows a screen shot from the computer controlling the electrodialysis apparatus utilizing the Metara Job Scheduler in accordance with an embodiment of the present invention. Thus, computer software may automatically select the concentration and composition of carrier solution depending on the nature of the matrix.

In one example, when the electrodialysis apparatus of the present invention is integrated with TCA to analyze metallic contaminants in a semiconductor processing bath, the following sequence of operations may be executed.

The "initializing dilution module hardware" operation cleans any spike residual left from a previous run and fills the syringes with fresh spike solution.

The "initializing mix module" operation cleans the mixing reservoirs and syringes where sample will be mixed with isotope spike.

The "cleaning membrane reservoir" operation cleans the residual sample from reservoir with air first and then with UPW.

The "clearing fluids from membrane" operation pushes air through the membrane via the sample syringe to clean any fluid left in the membrane.

In the mean time, the "sample extraction module" operation is initialized and the recipe of the job is loaded for execution.

After these operations, the apparatus of the present invention performs treatment of a sample solution to neutralize, eliminate, and/or modify the matrix and to stabilize any metals in solution in accordance with the inventive method described in detail above. Finally, the sample is delivered to an analytical instrument for analysis such as an electro spray mass spectrometer (ES-MS). It will be apparent that various analytical devices may be used within the scope of the present invention.

EXAMPLE 1

5% $H_2SO_4$ with known amount of spiked metals was passed through a Dionex CSRS electrodialysis apparatus with flow rate at about 600 μL per minute and current at about 300 mA. After the neutralization, the sample was analyzed by an Electro-spray Ion Trap Time of Flight Mass Spectrometer (ES ToF MS).

Table 1 below shows the percentage recovery of various spiked metals using different carboxylic acids as carrier solutions. When ultra pure water (UPW) was used as the carrier solution at a flow rate of about 4 ml per minute, there was no recovery for certain metals like titanium, chromium, iron, nickel, copper, and zinc. No baseline subtraction was calculated into the data, thereby resulting in some metals having a percentage recovery greater than 100%.

As is shown by the data in Table 1, using a metal-complexing reagent, such as carboxylic acid, in a carrier solution allows the detection of trace metals. It is also shown from the data in Table 1 that metals have different percentage recovery by changing one carboxylic acid for another.

TABLE 1

Sulfuric Acid Samples
Percentage Recovery based upon Matrix Match sample
(pass thru the membrane)

| | Carrier Solution | | | | | |
|---|---|---|---|---|---|---|
| Elements | UPW | Formic acid | Acetic acid | Oxalic Acid | Formic + Acetic acid | Glycolic acid |
| Ti46 | 0 | 57 | 11 | 93 | 67 | — |
| Cr53 | 0 | 102 | 84 | 111 | 91 | 65 |
| Fe57 | 0 | 19 | 14 | 5 | 99 | 133 |
| Ni62 | 0 | 109 | 63 | 40 | 204 | 85 |
| Cu65 | 0 | 2 | 1 | 5 | 13 | 82 |
| Zn68 | 0 | 57 | 37 | 60 | 41 | 48 |

Figure 10:
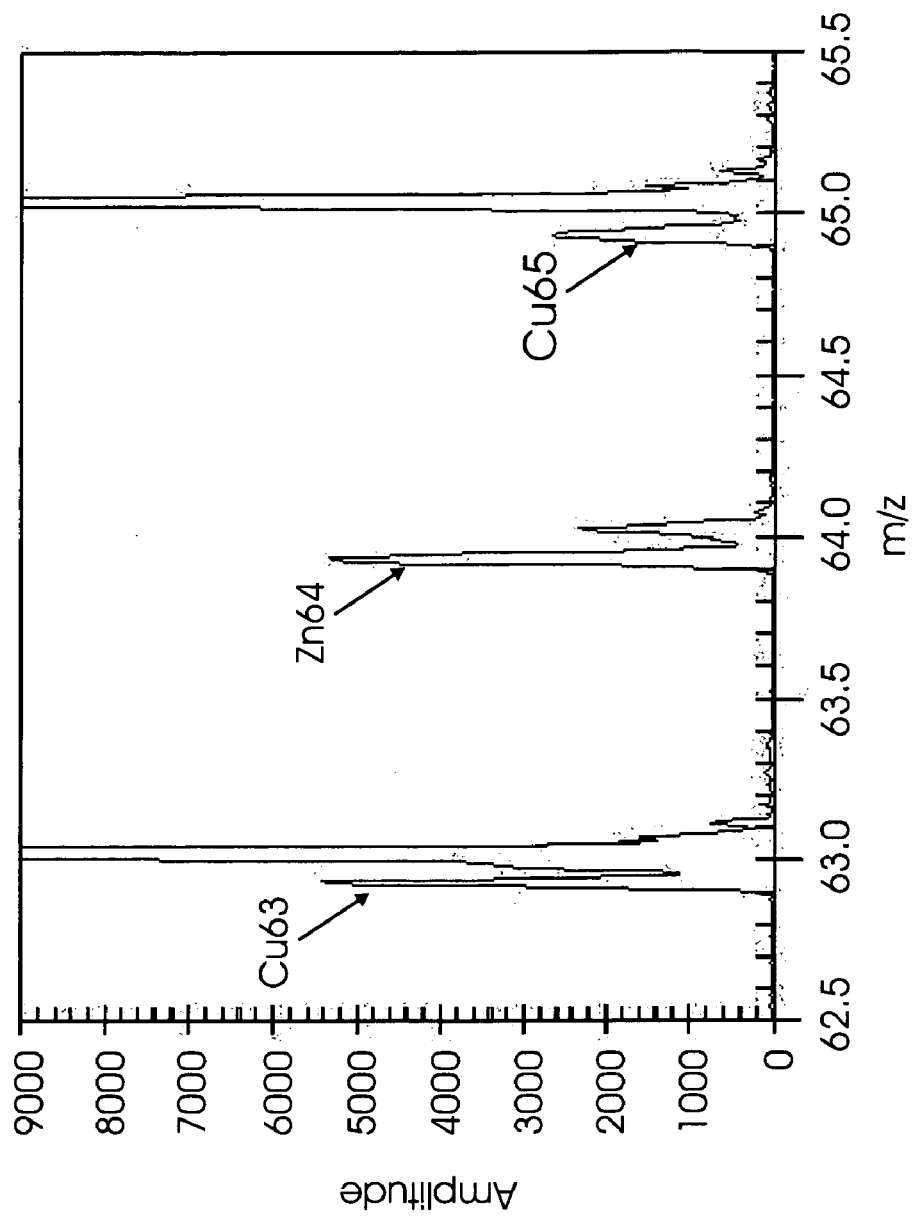
FIG. 10 is an illustrative example of a mass spectrum of trace metals in an $H_2SO_4$ matrix resulting from an embodiment of the present invention.

FIG. 10 shows an example of the elemental mass spectrum for copper and zinc in a sulfuric acid matrix utilizing a method and apparatus of the present invention.

EXAMPLE 2

5% buffered hydrofluoric acid ($NH_4F+HF$) with known amount of spiked metals was passed through a Dionex CSRS electrodialysis apparatus with flow rate at about 500 μL per minute and current at about 250 mA. The sample was recirculated 4 times through the electrodialysis apparatus. Ultra-pure-water (UPW) was used as the carrier solution at a flow rate of about 5 ml per minute. After neutralization, the sample solution was analyzed by an Electro-spray Ion Trap Time of Flight Mass Spectrometer (ES ToF MS).

Figure 11:
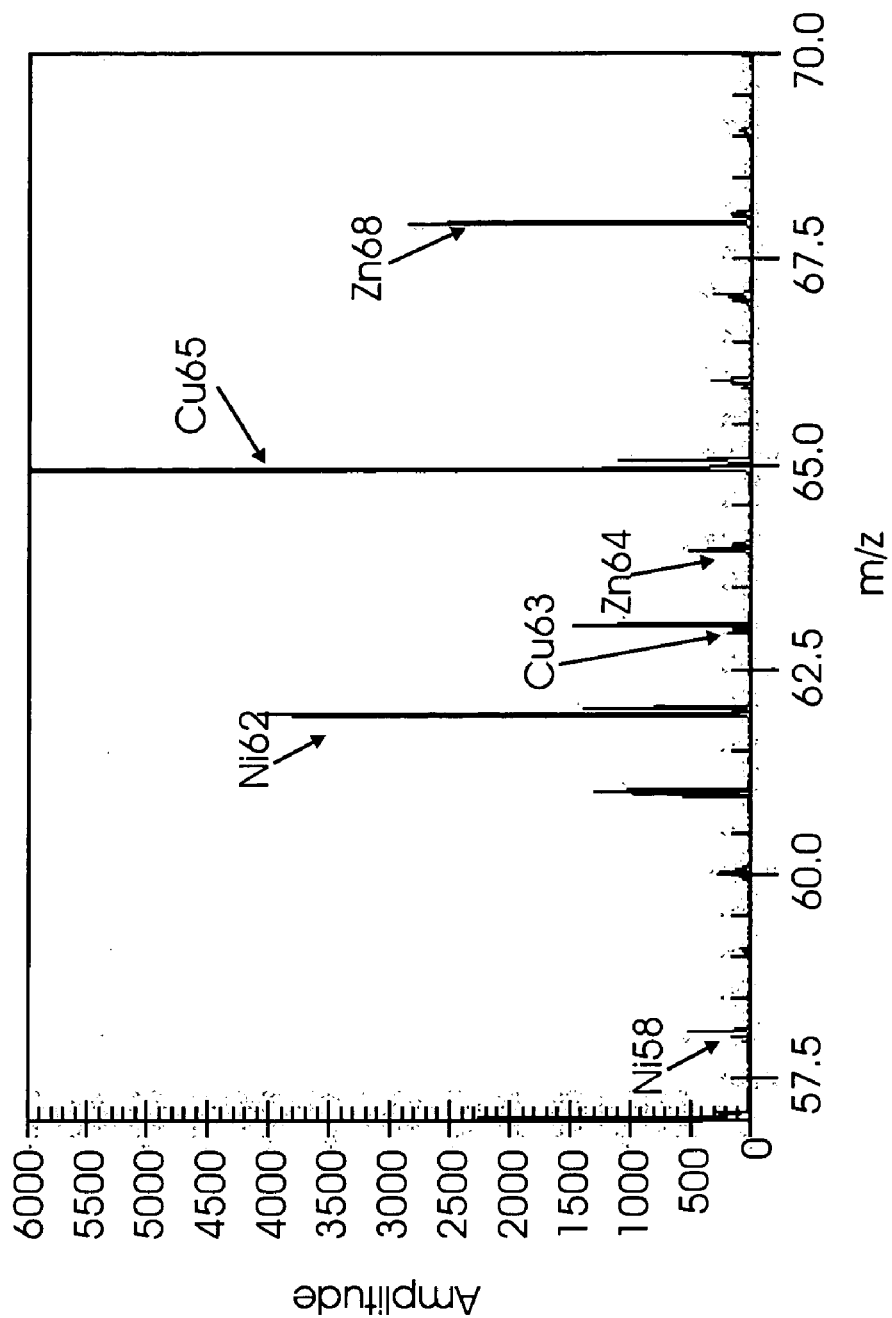
FIG. 11 is an illustrative example of a mass spectrum of trace metals in a buffered hydrofluoric acid matrix resulting from an embodiment of the present invention.

FIG. 11 shows an example of the elemental mass spectrum for various metals in a buffered hydrofluoric acid matrix utilizing a method and apparatus of the present invention.

The above-described embodiments of the present invention are merely meant to be illustrative and not limiting. Various changes and modifications may be made without departing from this invention in its broader aspects. Therefore, the appended claims encompass all such changes and modifications as falling within the true spirit and scope of this invention.

What is claimed is:

1. A method of analyzing trace metals in solution, comprising:
   providing a sample channel separated from a first carrier solution channel by a first anion exchange membrane and separated from a second carrier solution channel by a second anion exchange membrane;
   flowing a sample through the sample channel, wherein the sample includes an acidic matrix and at least one trace metal to be detected;
   flowing a first carrier solution through the first carrier solution channel;

flowing a second carrier solution including a metal-complexing reagent through the second carrier solution channel so that the metal-complexing reagent diffuses through the second ion exchange membrane into the sample; and providing an electrical potential to assist diffusion of an anionic form of the acidic matrix through the first anion exchange membrane into the first carrier solution channel and to assist diffusion of hydroxide ions from the second carrier solution through the second anion exchange membrane into the sample to neutralize at least a portion of the acidic matrix, whereby the diffused metal-complexing reagent in the sample complexes with the at least one trace metal such that the at least one trace metal doesn't combine with the hydroxide ions.

2. The method of claim 1, wherein the metal-complexing reagent is an organic or inorganic acid.

3. The method of claim 1, wherein the metal-complexing reagent is selected from the group consisting of formic acid, acetic acid, oxalic acid, glycolic acid, ethylenediaminetetraacetic acid (EDTA), nitrotriacetic acid (NTA), diethylenetriaminepentaacetic acid (DTPA), ethylenediamine (EDA), glycine, iminodiacetic acid (IDA), and amines.

4. The method of claim 1, further comprising detecting the complexed trace metal by mass spectroscopy.

5. A method of analyzing trace metals in solution, comprising:

providing a sample channel between two carrier solution channels, the sample channel being defined by two anion exchange membranes that separate the sample channel from the two carrier solution channels;

flowing a sample through the sample channel, wherein the sample includes an acidic matrix and at least one trace metal to be detected;

providing an electrical potential between the carrier solution channels to assist diffusion of an anionic form of the acidic matrix through a first one of the anion exchange membranes and to assist diffusion of hydroxide ions through a remaining one of the anion exchange membranes into the sample to neutralize at least a portion of the acidic matrix;

flowing a cater solution including at least one metal-complexing reagent through at least one of the two carrier solution channels so that the at least one metal-complexing reagent is diffused through at least one of the anion exchange membranes into the sample channel;

forming a metal complex between the at least one metal-complexing reagent and the at least one trace metal to stabilize the at least one trace metal in solution, thereby treating the sample; and detecting the stabilized trace metal in the treated sample.

6. The method of claim 5, wherein the metal-complexing reagent is an organic or inorganic acid.

7. The method of claim 5, wherein the metal-complexing reagent is selected from the group consisting of formic acid, acetic acid, oxalic acid, glycolic acid, ethylenediaminetetraacetic acid (EDTA), nitrotriacetic acid (NTA), diethylenetriaminepentaacetic acid (DTPA), ethylenediamine (EDA), glycine, iminodiacetic acid (IDA), and amines.

8. The method of claim 5, wherein the electrical potential is provided by an anode electrode and a cathode electrode in electrical communication with the two carrier solution channels.

9. The method of claim 5, wherein the detecting of the stabilized trace metal is performed by mass spectroscopy.

10. The method of claim 5, wherein water is flowed through the at least one of the two carrier solution channels and electrolyzed to generate hydroxide or hydronium ions.

11. The method of claim 5, further comprising re-flowing the treated sample through the sample channel for further treatment prior to analysis.

12. The method of claim 11, wherein the treated sample is stored in a heated reservoir prior to being re-flowed through the sample channel.

13. The method of claim 11, wherein the electrical potential is provided by an anode electrode and a cathode electrode in electrical communication with the two carrier solution channels.

14. The method of claim 13, wherein the polarity of the electrodes are switched between re-flow cycles of the treated sample through the sample channel.

15. The method of claim 5, further comprising recycling unspent metal-complexing reagent through the at least one of the two carrier solution channels.

16. The method of claim 5, further comprising flowing a different carrier solution through each of the two carrier solution channels.

17. The method of claim 16, wherein the carrier solution flowing through a carrier solution channel includes the at least one metal-complexing reagent and the carrier solution simultaneously flowing through the other carrier solution channel does not include a metal-complexing reagent.

18. The method of claim 5, wherein the anion exchange membranes are different from one another.

19. A method of analyzing trace metals in solution, comprising:

providing an electrodialysis apparatus including a sample channel between two carrier solution channels, the sample channel being defined by two anion exchange membranes that separate the sample channel from the two carrier solution channels;

flowing a sample through the sample channel, wherein the sample includes an acidic matrix and at least one trace metal to be detected;

providing an electrical potential between the carrier solution channels transverse to the flow of the sample through the sample channel to assist diffusion an anionic form of the acidic matrix through a first one of the anion exchange membranes and to assist diffusion of hydroxide ions through a remaining one of the anion exchange membranes into the sample to neutralize at least a portion of the acidic matrix;

flowing a carrier solution including at least one metal-complexing reagent through at least one of the two carrier solution channels so that the at least one metal-complexing reagent is diffused through at least one of the two anion exchange membranes into the sample channel;

forming a metal complex between the at least one metal-complexing reagent and the at least one trace metal to stabilize the at least one trace metal in solution, thereby treating the sample; and analyzing the treated sample by mass spectroscopy to detect the stabilized trace metal.

20. The method of claim 19, wherein the anion exchange membranes are different from one another.

* * * * *